United States Patent
D'Lima et al.

(10) Patent No.: US 10,179,193 B2
(45) Date of Patent: *Jan. 15, 2019

(54) METHODS OF TRANSPLANTING CHONDROCYTES

(71) Applicant: Scripps Health, San Diego, CA (US)

(72) Inventors: Darryl D. D'Lima, San Diego, CA (US); Tsaiwei Olee, San Diego, CA (US); Clifford W. Colwell, San Diego, CA (US)

(73) Assignee: SCRIPPS HEALTH, San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/872,667

(22) Filed: Jan. 16, 2018

(65) Prior Publication Data

US 2018/0154046 A1 Jun. 7, 2018

Related U.S. Application Data

(63) Continuation of application No. 14/438,583, filed as application No. PCT/US2013/067349 on Oct. 29, 2013, now Pat. No. 9,974,885.

(60) Provisional application No. 61/719,902, filed on Oct. 29, 2012.

(51) Int. Cl.
| | |
|---|---|
| *A61L 27/44* | (2006.01) |
| *A61L 27/26* | (2006.01) |
| *A61L 27/38* | (2006.01) |
| *A61L 27/54* | (2006.01) |

(52) U.S. Cl.
CPC .............. *A61L 27/44* (2013.01); *A61L 27/26* (2013.01); *A61L 27/3817* (2013.01); *A61L 27/3821* (2013.01); *A61L 27/54* (2013.01); *A61L 2300/412* (2013.01); *A61L 2300/64* (2013.01); *A61L 2430/02* (2013.01); *A61L 2430/06* (2013.01)

(58) Field of Classification Search
None
See application file for complete search history.

(56) References Cited

U.S. PATENT DOCUMENTS

| | | | |
|---|---|---|---|
| 5,399,347 | A | 3/1995 | Trentham et al. |
| 5,645,851 | A | 7/1997 | Moore |
| 5,843,780 | A | 12/1998 | Thomson |
| 6,025,327 | A | 2/2000 | Alkayali |
| 6,200,806 | B1 | 3/2001 | Thomson |
| 6,323,319 | B1 | 11/2001 | Alkayali |
| 6,511,958 | B1 | 1/2003 | Atkinson et al. |
| 6,780,841 | B2 | 8/2004 | Ishaq |
| 2002/0090391 | A1 | 7/2002 | Geistlich et al. |
| 2003/0026786 | A1 | 2/2003 | Pittenger et al. |
| 2003/0091652 | A1 | 5/2003 | Ishaq |
| 2003/0152556 | A1 | 8/2003 | Lai et al. |
| 2004/0213852 | A1 | 10/2004 | Van Kuppevelt et al. |
| 2006/0068496 | A1 | 3/2006 | Kelly |
| 2006/0189840 | A1 | 8/2006 | Walsh et al. |
| 2006/0239980 | A1 | 10/2006 | Bernad Miana et al. |
| 2007/0293427 | A1 | 12/2007 | Vouland et al. |
| 2008/0260694 | A1 | 10/2008 | Gronthos et al. |
| 2009/0029912 | A1 | 1/2009 | Gronthos et al. |
| 2010/0047212 | A1 | 2/2010 | Farinas et al. |
| 2011/0064810 | A1 | 3/2011 | Ghanavi |
| 2011/0256109 | A1 | 10/2011 | Noble et al. |
| 2012/0034271 | A1 | 2/2012 | Shu |
| 2012/0100103 | A1 | 4/2012 | Park et al. |
| 2015/0259648 | A1 | 9/2015 | D'Lima et al. |
| 2015/0275181 | A1 | 10/2015 | D'Lima et al. |
| 2015/0283303 | A1 | 10/2015 | D'Lima et al. |
| 2016/0040123 | A1 | 2/2016 | Kanemura et al. |

FOREIGN PATENT DOCUMENTS

| | | |
|---|---|---|
| CN | 101810855 A | 8/2010 |
| CN | 101934092 A | 1/2011 |
| EP | 1312383 A2 | 5/2003 |
| JP | 2011015662 A | 1/2011 |
| KR | 20120046430 A | 5/2012 |
| WO | WO-2011065661 A2 | 6/2011 |
| WO | WO-2011066403 A1 | 6/2011 |
| WO | WO-2011091475 A1 | 8/2011 |
| WO | WO-2011123572 A1 | 10/2011 |
| WO | WO-2011124894 A1 | 10/2011 |
| WO | WO-2012013969 A1 | 2/2012 |
| WO | WO-2012126824 A1 | 9/2012 |
| WO | WO-2014052912 A1 | 4/2014 |
| WO | WO-2014070796 A1 | 5/2014 |
| WO | WO-2014070797 A1 | 5/2014 |

OTHER PUBLICATIONS

Barberi et al. Derivation of multipotent mesenchymal precursors from human embryonic stem cells. PLoS Med 2(6):e161 (2005).
Bian et al. Enhanced MSC Chondrogenesis Following Delivery of TGF-63 from Alginate Microspheres within Hyaluronic Acid Hydrogels In Vitro and In Vivo. Biomaterials 32(27):6425-6434 (2011).
Boeuf et al. Subtractive gene expression profiling of articular cartilage and mesenchymal stem cells: serpins as cartilage-relevant differentiation markers. Osteoarthritis and Cartilage 16(1):48-60 (2008).
Buska et al. The compressive strength properties of mineral wool slabs: Influence of structure anisotropy and methodical factors. Journal of Civil Engineering and Management 13:2, 97-106 (2007).
Calderon et al. Type II collagen-hyaluronan hydrogel—a step towards a scaffold for intervertebral disc tissue engineering. Eur Cell Mater 20:134-148 (2010).
Co-pending U.S. Appl. No. 15/872,577, filed Jan. 16, 2016.

(Continued)

*Primary Examiner* — Thomas J. Visone
(74) *Attorney, Agent, or Firm* — Wilson Sonsini Goodrich & Rosati

(57) ABSTRACT

Provided are tri-component matrices having collagen, hyaluronan, and chondroitin sulfate. Also provided are processes for producing a tri-component matrix. Additionally, provided are processes for providing cells capable of producing cartilage to a bone or cartilage defects.

20 Claims, 4 Drawing Sheets

(56) References Cited

OTHER PUBLICATIONS

Crowley et al. Safety and efficacy of undenatured type II collagen in the treatment of osteoarthritis of the knee: a clinical trial. Int J Med Sci 6(6):312-321 (2009).
Davidenko et al. Collagen-hyaluronic acid scaffolds for adipose tissue engineering. Acta Biomater 6(10):3957-3968 (2010).
Dawson et al. Pigment epithelium-derived factor: a potent inhibitor of angiogenesis. Science 285(5425):245-248 (1999).
Elshal et al. The multi-kinase inhibitor pazopanib targets hepatic stellate cell activation and apoptosis alleviating progression of liver fibrosis. Naunyn Schmiedebergs Arch Pharmacol 388(12):1293-1304 (2015).
Even-Ram et al. Matrix control of stem cell fate. Cell 126(4):645-647 (2006).
Feng et al. Molecules that promote or enhance reprogramming of somatic cells to induced pluripotent stem cells. Cell Stem Cell 4(4):301-312 (2009).
Gong et al. Direct and progressive differentiation of human embryonic stem cells into the chondrogenic lineage. J Cell Physiol 224:664-671 (2010).
Guo et al. Hydrogels of collagen/chondroitin sulfate/hyaluronan interpenetrating polymer network for cartilage tissue engineering. J Mater Sci Mater Med 23(9):2267-2279 (2012).
Jihong et al. A potential use of collagen-hyaluronan-chondroitin sulfate tri-copolymer scaffold for cartilage tissue engineering. Zhongguo Xiu Fu Chong Jian Wai Ke Za Zhi 20(2):130-133 Database Accession No. NLM16529321 (1 pg.) (2006).
Kawasaki et al. Hyaluronic acid enhances proliferation and chondroitin sulfate synthesis in cultured chondrocytes embedded in collagen gels. J Cell Physiol 179(2):142-148 (1999).
Kim et al. Generation of human induced pluripotent stem cells from osteoarthritis patient-derived synovial cells. Arthritis Rheum 63(10):3010-3021 (2011).
Ko et al. Genipin cross-linking of type II collagen-chondroitin sulfate-hyaluronan scaffold for articular cartilage therapy. J Med Biol Eng 27(1):7-14 (2007).
Ko et al. Type II collagen-chondroitin sulfate-hyaluronan scaffold cross-linked by genipin for cartilage tissue engineering. J Biosci Bioeng 107(2):177-182 (2009).
Lacerdo-Pinheiro et al. Concomitant Multipotent and Unipotent Dental Pulp Progenitors and Their Respective Contribution to Mineralised Tissue Formation. European Cells and Materials 23(371-386) (2012).
Li et al. Construction of collagen II/hyaluronate/chondroitin-6-sulfate tri-copolymer scaffold for nucleus pulposus tissue engineering and preliminary analysis of its physico-chemical properties and biocompatibility. J Mater Sci. 21:741-751 (2010).
Liu et al. One-step derivation of mesenchymal stem cell (MSC)-like cells from human pluripotent stem cells on a fibrillar collagen coating. PLos One 7(3):e33225 (2012).
Nagler-Anderson et al. Suppression of type II collagen-induced arthritis by intragastric administration of soluble type II collagen. PNAS USA 83:7443-7746 (1986).
Nishimoto et al. Effect of chondroitin sulfate and hyaluronic acid on gene expression in a three-dimensional culture of chondrocytes. J Biosci Bioeng 100(1):123-126 (2005).
Nyberg et al. Endogenous inhibitors of angiogenesis. Cancer Res 65(10):3967-3979 (2005).
Oh et al. Methods for Expansion of Human Embryonic Stem Cells. Stem Cells 23(5):605-609 (2005).
Oldershaw et al. Directed differentiation of human embryonic stem cells toward chondrocytes. Nat Biotechol 28(11):1187-1194 (2010).
PCT/US2013/062437 International Preliminary Report on Patentability dated Apr. 9, 2015.
PCT/US2013/062437 International Search Report and Written Opinion dated Jan. 14, 2014.
PCT/US2013/067349 International Preliminary Report on Patentability dated May 14, 2015.
PCT/US2013/067349 International Search Report and Written Opinion dated Dec. 20, 2013.
PCT/US2013/067350 International Preliminary Report on Patentability dated May 14, 2015.
PCT/US2013/067350 International Search Report and Written Opinion dated Jan. 28, 2014.
Peal et al. Therapeutic efficacy and safety of undenatured type-II collagen (UC-II) alone or in combination with (−)-hydroxycitric acid and chromemate in arthritic dogs. J Vet Phrmacol Therap 30:275-278 (2007).
Pfander et al. Pigment epithelium derived factor—the product of the EPC-1 gene—is expressed by articular chondrocytes and up regulated in osteoarthritis. Ann Rheum Dis 65(7):965-967 (2006).
Pieper et al. Crosslinked type II collagen matrices: preparation, characterization, and potential for cartilage engineering. Biomaterials 23:3183-3192 (2002).
Poliard et al. Controlled Conversion of an Immortalized Mesodermal Progenitor Cell Towards Osteogenic, Chondrogenic, or Adipogenic Pathways. The Journal of Cell Biology 130(6):1461-1472 (1995).
Quan et al. Localization of pigment epithelium-derived factor in growing mouse bone. Calcif Tissue Int 76(2):146-153 (2005).
Raghunath et al. Advancing cartilage tissue engineering: the application of stem cell technology. Curr Opin Biotechnol 16(5):503-509 (2005).
Schauss et al. Acute and subchronic oral toxicity studies in rats of a hydrolyzed chicken sternal cartilage preparation. Food Chem Toxicol 45:315-321 (2007).
Senju et al. Generation of dendritic cells and macrophages from human induced pluripotent stem cells aiming at cell therapy. Gene Ther 18(9):874-883 (2011).
Sheu et al. Characterization of collagen gel solutions and collagen matrices for cell culture. Biomaterials 22:1713-1719 (2001).
Takahashi et al. Induction of Pluripotent Stem Cells from Adult Human Fibroblasts by Defined Factors. Cell 131:861-872 (2007).
Thomson et al. Embryonic stem cell lines derived from human blastocysts. Science 282(5391):1145-1147 (1998).
Thomson et al. Isolation of a primate embryonic stem cell line. PNAS USA 92(17):7844-7848 (1995).
Thomson et al. Primate embryonic stem cells. Curr Top Dev Biol 38:133-165 (1998).
Tse et al. Stiffness gradients mimicking in vivo tissue variation regulate mesenchymal stem cell fate. PLoS One 6(1):e15978 (2011).
U.S. Appl. No. 14/431,893 Office Action dated Mar. 22, 2017.
U.S. Appl. No. 14/431,893 Office Action dated Sep. 26, 2017.
U.S. Appl. No. 14/438,581 Office Action dated Jan. 9, 2017.
U.S. Appl. No. 14/438,581 Office Action dated Jul. 31, 2017.
U.S. Appl. No. 14/438,581 Office Action dated Sep. 30, 2016.
U.S. Appl. No. 14/438,583 Office Action dated Apr. 13, 2017.
U.S. Appl. No. 14/438,583 Office Action dated Jul. 24, 2017.
U.S. Appl. No. 14/438,583 Office Action dated Sep. 30, 2016.
Wei et al. Chondrogenic differentiation of induced pluripotent stem cells from osteoarthritic chondrocytes in alginate matrix. Eur Cell Mater 23:1-12 (2012).
Wu et al. Generation of Induced Pluripotent Stem Cells by Reprogramming Human Fibroblasts with the Stemgent Human TF Lentivirus Set. J Vis Exp (34):1553 (3 pgs.) (2009).
Yang et al. Stage-dependent effect of TGF-beta1 on chondrogenic differentiation of human embryonic stem cells. Stem Cells Dev 18(6):929-940 (2009).
Zahabi et al. A new efficient protocol for directed differentiation of retinal pigmented epithelial cells from normal and retinal disease induced pluripotent stem cells. Stem Cells Dev 21(12):2262-2272 (2012).
Zhang et al. Preparation of collagen—chondroitin sulfate—hyaluronic acid hybrid hydrogel scaffolds and cell compatibility in vitro. Carbohydrate Polymers 84:118-125 (2011).
Zheng et al. Chondrogenic differentiation of mesenchymal stem cells induced by collagen-based hydrogel: An in vivo study. J Biomed Mater Res 93A:783-792 (2010).
Huang et al. Collagen II/hyaluronan/chondroitin-6-sulfate tri-copolymer scaffold for nucleus pulposus tissue engineering. J Biomed Mater Res B Appl Biomater 92(2):322-331 (2010).

(56) References Cited

OTHER PUBLICATIONS

Okita et al. Generation of mouse induced pluripotent stem cells without viral vectors. Science 322(5903):949-953 (2008).

Omlor et al. Injection of a polymerized hyaluronic acid/collagen hydrogel matrix in an in vivo porcine disc degeneration model. Eur Spine J 21:1700-1708 (2012).

Bigdeli et al. Adaptation of human embryonic stem cells to feeder-free and matrix-free culture conditions directly on plastic surfaces. J Biotech 133:146-153 (2008).

U.S. Appl. No. 14/431,893 Office Action dated Nov. 9, 2018.

U.S. Appl. No. 15/872,577 Office Action dated Aug. 27, 2018.

METHODS OF TRANSPLANTING CHONDROCYTES

CROSS-REFERENCE

This application is a continuation of U.S. application Ser. No. 14/438,583, filed Apr. 24, 2015, which is a U.S. National Stage entry of International Application No. PCT/US2013/067349, filed Oct. 29, 2013, which claims the benefit of U.S. Application Ser. No. 61/719,902, filed Oct. 29, 2012, all of which are herein incorporated by reference in their entireties.

SUMMARY OF THE INVENTION

Disclosed herein, in some embodiments, is a tri-component matrix comprising: a) isolated and purified non-denatured type II collagen; b) hyaluronan; and c) chondroitin sulfate. In some embodiments, the tri-component matrix further comprises water. In some embodiments, the tri-component matrix further comprises a basal media. In some embodiments, the basal media is Medium 199. In some embodiments, the type II collagen is bovine-derived type II collagen. In some embodiments, the concentration of type II collagen is from about 0.5 mg/ml to about 5 mg/ml. In some embodiments, the concentration of type II collagen is about 3 mg/ml. In some embodiments, the concentration of hyaluronan is from about 0.25 mg/ml to about 3 mg/ml. In some embodiments, the concentration of hyaluronan is about 1 mg/ml. In some embodiments, the concentration of chondroitin sulfate is from about 0.25 mg/ml to about 3 mg/ml. In some embodiments, the concentration of chondroitin sulfate is about 1 mg/ml. In some embodiments, the tri-component matrix further comprises chondrocytes, chondroprogenitor cells, mesenchymal stem cells, induced pluripotent stem cells (iPS cells), iPS cells derived from chondrocytes, H9-derived chondroprogenitor cells, Sox-9 transduced chondrocytes, osteoblasts, osteoprogenitors, or any combinations thereof. In some embodiments, the tri-component matrix further comprises chondrocytes. In some embodiments, the tri-component matrix further comprises chondroprogenitor cells. In some embodiments, the tri-component matrix further comprises iPS cells.

Disclosed herein, in some embodiments, is a process for producing a transplantation composition for cartilage engineering comprising: a) dissolving isolated and purified non-denatured type II collagen in a solution comprising an acid, wherein the final concentration of type II collagen is from about 0.5 mg/ml to about 5 mg/ml; b) neutralizing the acid; c) adding from about 0.25 mg/ml to about 3 mg/ml of hyaluronan; and d) adding from about 0.25 mg/ml to about 3 mg/ml of chondroitin sulfate, wherein a tri-component matrix is produced. In some embodiments, the acid is acetic acid. In some embodiments, the acetic acid is at a concentration of about 0.01 M. In some embodiments, the acetic acid is neutralized with $NaHCO_3$/HEPES. In some embodiments, the tri-component matrix comprises Medium 199. In some embodiments, the hyaluronan is added at a concentration of about 1 mg/ml. In some embodiments, the chondroitin sulfate is added at a concentration of about 1 mg/ml. In some embodiments, the final concentration of type II collagen is about 3 mg/ml. In some embodiments, the process further comprises adding chondrocytes, chondroprogenitor cells, mesenchymal stem cells, iPS cells, iPS cells derived from chondrocytes, H9-derived chondroprogenitor cells, Sox-9 transduced chondrocytes, or any combinations thereof, to the tri-component matrix. In some embodiments, the process further comprises adding chondrocytes to the tri-component matrix. In some embodiments, the process further comprises adding chondroprogenitor cells to the tri-component matrix. In some embodiments, the process further comprises adding iPS cells to the tri-component matrix.

Disclosed herein, in some embodiments, is a method for inducing endogenous cartilage growth in a subject in need thereof, including the step of implanting in the subject a tri-component matrix as disclosed herein.

Disclosed herein, in some embodiments, is a method of treating a bone or cartilage defect in a subject in need thereof, comprising administering a transplantation composition comprising: i) a tri-component matrix, as disclosed herein, and ii) a population of cells, at the site of the bone or cartilage defect. In some embodiments, the population of cells comprises chondrocytes, chondroprogenitor cells, iPS cells, mesenchymal stem cells, osteoblasts, osteoprogenitors, or combinations thereof. In some embodiments, new tissue is produced. In some embodiments, the new tissue restores the surface of the cartilage or bone. In some embodiments, the new tissue comprises collagen type II. In some embodiments, the new tissue comprises superficial, intermediate, and deep zones characteristic of normal articular cartilage. In some embodiments, the superficial zone of the new tissue comprises lubricin. In some embodiments, the new tissue does not comprise teratomas, neoplastic cells, evidence of deformation, abnormal architectural features, or other inappropriate cell types. In some embodiments, the population of cells comprises chondrocytes. In some embodiments, the population of cells comprises chondroprogenitor cells. In some embodiments, the population of cells comprises iPS cells. In some embodiments, the iPS cells are derived from chondrocytes. In some embodiments, the chondroprogenitor cells are H9-derived chondroprogenitor cells. In some embodiments, the chondrocytes are Sox-9 transduced chondrocytes.

Disclosed herein, in some embodiments, is a method of treating a cartilage-related disorder in a subject in need thereof, comprising administering a mixture of a tri-component matrix, as claimed in claim 1, and chondrocytes, chondroprogenitor cells, mesenchymal stem cells, iPS cells, iPS cells derived from chondrocytes, H9-derived chondroprogenitor cells, Sox-9 transduced chondrocytes, osteoblasts, osteoprogenitors, or any combinations thereof, to a site of cartilage injury or defect. In some embodiments, the cartilage-related disorder is articular cartilage trauma, meniscus injury, a chonodrogenesis disorder, arthritis, chondropathy, chondrosarcoma, chondromalacia, polychondritis, relapsing polychondritis, slipped epiphysis, osteochondritis dissecans, chondrodysplasia, costochondritis, osteochondroma, spondylosis, osteochondroses, Tietze syndrome, dermochondrocorneal dystrophy of Francois, epiphyseal dysplasia, carpotarsal osteochondromatosis, achondropasia, chondrocalcinosis, genochondromatosis, chondroma, achondrogenesis, echondromata, hyprochondroplasia, or Keutel syndrome. In some embodiments, the cartilage-related disorder is arthritis. In some embodiments, the arthritis is osteoarthritis. In some embodiments, the osteoarthritis occurs in the knee, finger, wrist, hip, spine, shoulder, elbow, toe, ankle, or neck of a subject.

Disclosed herein, in some embodiments, is a cartilage repair implant comprising: a) a tri-component matrix, as disclosed herein; and b) cells selected from chondrocytes, chondroprogenitor cells, mesenchymal stem cells, iPS cells, iPS cells derived from chondrocytes, H9-derived chondroprogenitor cells, Sox-9 transduced chondrocytes, osteoblasts, osteoprogenitors, or any combinations thereof. In some embodiments, the cartilage repair implant further comprises a biomaterial substrate, wherein the biomaterial substrate is selected from: polyglycolic acid (PGA), polylactic acid, alginates, polyethylene oxide, fibrin adhesive, polylactic acid-polyglycolic acid copolymer, human dermis, a membrane such as a sheet, a porous body such as sponges, a mesh such as a knit, a textile, a non-woven fabric, cotton, porous material, or combinations thereof.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
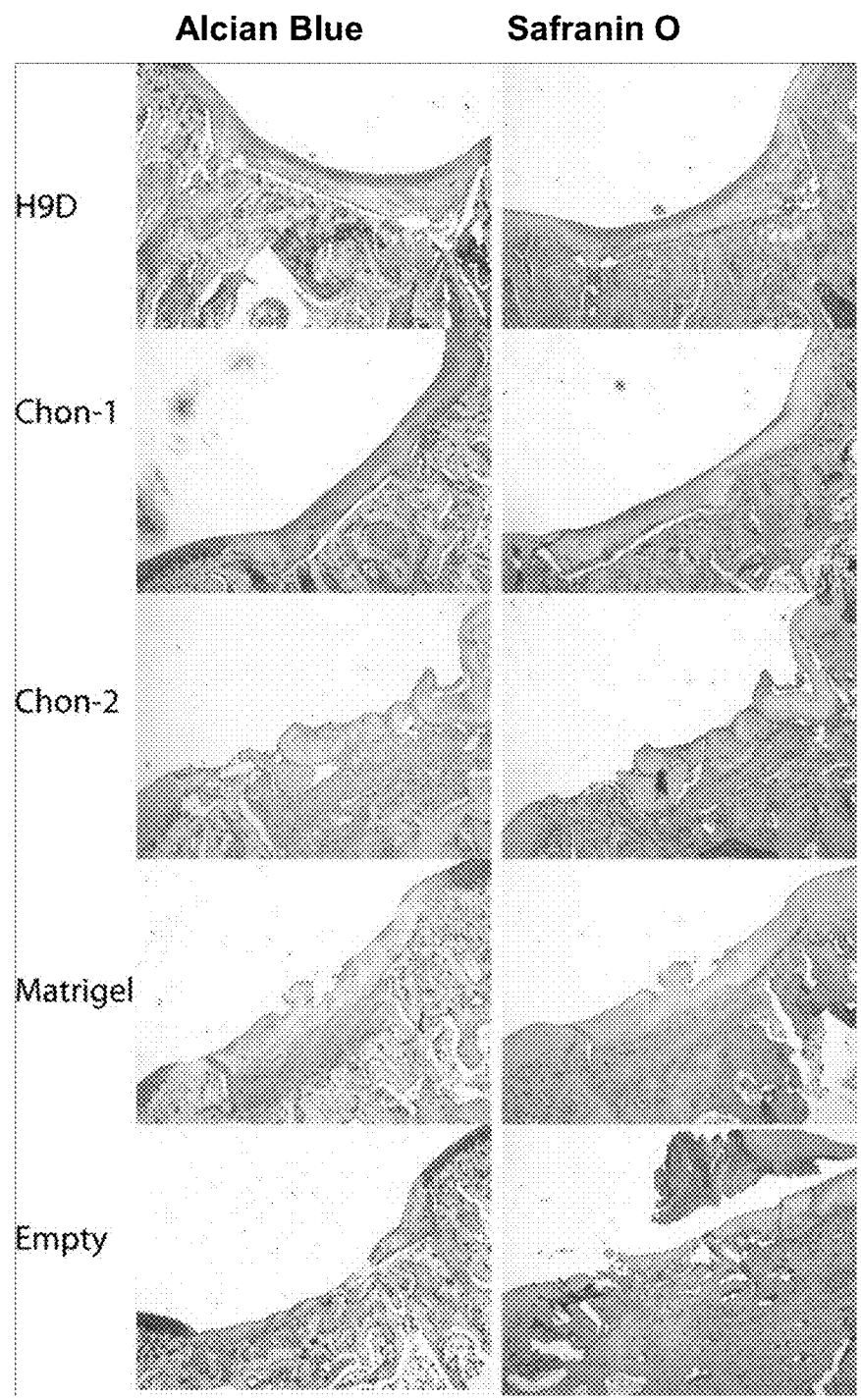
FIG. 1 exemplifies tissue repair by H9-derived chondroprogenitors and chondroprogenitors derived from adult human chondrocytes (CHON-1 and CHON-2). Alcian Blue and Safranin O staining was comparable between the H9-derived chondroprogenitors and the chondroprogenitors derived from adult human chondrocytes. Poor tissue repair was seen in empty osteochondral defects or osteochondral defects filled with only Matrigel.

Disclosed herein, in some embodiments, is a tri-component matrix comprising: a) isolated and purified non-denatured type II collagen; b) hyaluronan; and c) chondroitin sulfate. In some embodiments, the tri-component matrix further comprises water. In some embodiments, the tri-component matrix further comprises a basal media. In some embodiments, the basal media is Medium 199. In some embodiments, the type II collagen is bovine-derived type II collagen. In some embodiments, the concentration of type II collagen is from about 0.5 mg/ml to about 5 mg/ml. In some embodiments, the concentration of type II collagen is about 3 mg/ml. In some embodiments, the concentration of hyaluronan is from about 0.25 mg/ml to about 3 mg/ml. In some embodiments, the concentration of hyaluronan is about 1 mg/ml. In some embodiments, the concentration of chondroitin sulfate is from about 0.25 mg/ml to about 3 mg/ml. In some embodiments, the concentration of chondroitin sulfate is about 1 mg/ml. In some embodiments, the tri-component matrix further comprises chondrocytes, chondroprogenitor cells, mesenchymal stem cells, induced pluripotent stem cells (iPS cells), iPS cells derived from chondrocytes, H9-derived chondroprogenitor cells, Sox-9 transduced chondrocytes, osteoblasts, osteoprogenitors, or any combinations thereof. In some embodiments, the tri-component matrix further comprises chondrocytes. In some embodiments, the tri-component matrix further comprises chondroprogenitor cells. In some embodiments, the tri-component matrix further comprises iPS cells.

Disclosed herein, in some embodiments, is a process for producing a transplantation composition for cartilage engineering comprising: a) dissolving isolated and purified non-denatured type II collagen in a solution comprising an acid, wherein the final concentration of type II collagen is from about 0.5 mg/ml to about 5 mg/ml; b) neutralizing the acid; c) adding from about 0.25 mg/ml to about 3 mg/ml of hyaluronan; and d) adding from about 0.25 mg/ml to about 3 mg/ml of chondroitin sulfate, wherein a tri-component matrix is produced. In some embodiments, the acid is acetic acid. In some embodiments, the acetic acid is at a concentration of about 0.01 M. In some embodiments, the acetic acid is neutralized with $NaHCO_3$/HEPES. In some embodiments, the tri-component matrix comprises Medium 199. In some embodiments, the hyaluronan is added at a concentration of about 1 mg/ml. In some embodiments, the chondroitin sulfate is added at a concentration of about 1 mg/ml. In some embodiments, the final concentration of type II collagen is about 3 mg/ml. In some embodiments, the process further comprises adding chondrocytes, chondroprogenitor cells, mesenchymal stem cells, iPS cells, iPS cells derived from chondrocytes, H9-derived chondroprogenitor cells, Sox-9 transduced chondrocytes, or any combinations thereof, to the tri-component matrix. In some embodiments, the process further comprises adding chondrocytes to the tri-component matrix. In some embodiments, the process further comprises adding chondroprogenitor cells to the tri-component matrix. In some embodiments, the process further comprises adding iPS cells to the tri-component matrix.

Disclosed herein, in some embodiments, is a method for inducing endogenous cartilage growth in a subject in need thereof, including the step of implanting in the subject a tri-component matrix as disclosed herein.

Disclosed herein, in some embodiments, is a method of treating a bone or cartilage defect in a subject in need thereof, comprising administering a transplantation composition comprising: i) a tri-component matrix, as disclosed herein, and ii) a population of cells, at the site of the bone or cartilage defect. In some embodiments, the population of cells comprises chondrocytes, chondroprogenitor cells, iPS cells, mesenchymal stem cells, osteoblasts, osteoprogenitors, or combinations thereof. In some embodiments, new tissue is produced. In some embodiments, the new tissue restores the surface of the cartilage or bone. In some embodiments, the new tissue comprises collagen type II. In some embodiments, the new tissue comprises superficial, intermediate, and deep zones characteristic of normal articular cartilage. In some embodiments, the superficial zone of the new tissue comprises lubricin. In some embodiments, the new tissue does not comprise teratomas, neoplastic cells, evidence of deformation, abnormal architectural features, or other inappropriate cell types. In some embodiments, the population of cells comprises chondrocytes. In some embodiments, the population of cells comprises chondroprogenitor cells. In some embodiments, the population of cells comprises iPS cells. In some embodiments, the iPS cells are derived from chondrocytes. In some embodiments, the chondroprogenitor cells are H9-derived chondroprogenitor cells. In some embodiments, the chondrocytes are Sox-9 transduced chondrocytes.

Disclosed herein, in some embodiments, is a method of treating a cartilage-related disorder in a subject in need thereof, comprising administering a mixture of a tri-component matrix, as claimed in claim 1, and chondrocytes, chondroprogenitor cells, mesenchymal stem cells, iPS cells, iPS cells derived from chondrocytes, H9-derived chondroprogenitor cells, Sox-9 transduced chondrocytes, osteoblasts, osteoprogenitors, or any combinations thereof, to a site of cartilage injury or defect. In some embodiments, the cartilage-related disorder is articular cartilage trauma, meniscus injury, a chonodrogenesis disorder, arthritis, chondropathy, chondrosarcoma, chondromalacia, polychondritis, relapsing polychondritis, slipped epiphysis, osteochondritis dissecans, chondrodysplasia, costochondritis, osteochondroma, spondylosis, osteochondroses, Tietze syndrome, dermochondrocorneal dystrophy of Francois, epiphyseal dysplasia, carpotarsal osteochondromatosis, achondropasia, chondrocalcinosis, genochondromatosis, chondroma, achondrogenesis, echondromata, hypochondroplasia, or Keutel syndrome. In some embodiments, the cartilage-related disorder is arthritis. In some embodiments, the arthritis is osteoarthritis. In some embodiments, the osteoarthritis occurs in the knee, finger, wrist, hip, spine, shoulder, elbow, toe, ankle, or neck of a subject.

Disclosed herein, in some embodiments, is a cartilage repair implant comprising: a) a tri-component matrix, as disclosed herein; and b) cells selected from chondrocytes, chondroprogenitor cells, mesenchymal stem cells, iPS cells, iPS cells derived from chondrocytes, H9-derived chondroprogenitor cells, Sox-9 transduced chondrocytes, osteoblasts, osteoprogenitors, or any combinations thereof. In some embodiments, the cartilage repair implant further comprises a biomaterial substrate, wherein the biomaterial substrate is selected from: polyglycolic acid (PGA), polylactic acid, alginates, polyethylene oxide, fibrin adhesive, polylactic acid-polyglycolic acid copolymer, human dermis, a membrane such as a sheet, a porous body such as sponges, a mesh such as a knit, a textile, a non-woven fabric, cotton, porous material, or combinations thereof.

Cartilage

Articular cartilage is a type of hyaline cartilage that lines the surfaces of the opposing bones in a diarthrodial joint (e.g. knee, hip, shoulder, etc.). Articular cartilage provides a near-frictionless articulation between the bones, while also functioning to absorb and transmit the compressive and shear forces encountered in the joint. Further, since the tissue associated with articular cartilage is aneural, these load absorbing and transmitting functions occur in a painless fashion in a healthy joint.

Fibrocartilage is found in diarthrodial joints, symphyseal joints, intervertebral discs, articular discs, as inclusions in certain tendons that wrap around a pulley, and at insertion sites of ligaments and tendons into bone. Made of a mixture of collagen type I and type II fibers, fibrocartilage may be damaged, causing pain in the affected joint.

It is understood for purposes of this application that the term "cartilage" includes articular cartilage and fibrocartilage.

Tri-Component Implant Matrix

Disclosed herein are novel materials useful for medical grafting and cell culture, and methods for making and using them. Additional embodiments as well as features and advantages of the invention will be apparent from the descriptions herein.

Disclosed herein, in some embodiments, is a tri-component matrix. In some embodiments, the tri-component matrix comprises collagen; hyaluronan; and chondroitin sulfate. In some embodiments, the collagen is type II collagen. In some embodiments, the collagen is non-denatured. In some embodiments, the tri-component matrix further comprises water.

In some embodiments, the tri-component matrix further comprises chondrocytes or chondroprogenitor cells. In some embodiments, the tri-component matrix further comprises mesenchymal stem cells. In some embodiments, the tri-component matrix further comprises induced pluripotent stem (iPS) cells. In some embodiments, the tri-component matrix further comprises iPS cells derived from chondrocytes. In some embodiments, the tri-component matrix further comprises H9-derived chondroprogenitor cells. In some embodiments, the tri-component matrix further comprises Sox-9 transduced chondrocytes.

In some embodiments, the tri-component matrix is a gel. In some embodiments, the tri-component matrix is a molded solid. In some embodiments, the tri-component matrix is a liquid.

In some embodiments, the tri-component matrix further comprises a basal media. In some embodiments, the basal media is Medium 199, DMEM (for example, DMEM supplemented with fetal bovine serum), RPMI-1640, Ham's F-12, or any combinations thereof. In some embodiments, the basal media is a chondrocyte basal medium. In some embodiments, the basal media comprises the following components: Glycine; L-Alanine; L-Arginine hydrochloride; L-Aspartic acid; L-Cysteine hydrochloride-$H_2O$; L-Cystine 2HCl; L-Glutamic Acid; L-Glutamine; L-Histidine hydrochloride-$H_2O$; L-Hydroxyproline; L-Isoleucine; L-Leucine; L-Lysine hydrochloride; L-Methionine; L-Phenylalanine; L-Proline; L-Serine; L-Threonine; L-Tryptophan; L-Tyrosine disodium salt dehydrate; L-Valine; Alpha-tocopherol Phosphate; Ascorbic Acid; Biotin; Choline chloride; D-Calcium pantothenate; Folic Acid; Menadione (Vitamin K3); Niacinamide; Nicotinic acid (Niacin); Para-Aminobenzoic Acid; Pyridoxal hydrochloride; Pyridoxine hydrochloride; Riboflavin; Thiamine hydrochloride; Vitamin A (acetate); Vitamin D2 (Calciferol); i-Inositol; Calcium Chloride ($CaCl_2$) (anhyd.); Ferric nitrate ($Fe(NO_3)$—$9H_2O$); Magnesium Sulfate ($MgSO_4$) (anhyd.); Potassium Chloride (KCl); Sodium Bicarbonate ($NaHCO_3$); Sodium Chloride (NaCl); Sodium Phosphate monobasic ($NaH_2PO_4$—$H_2O$); 2-deoxy-D-ribose; Adenine sulfate; Adenosine 5'-phosphate; Adenosine 5'-triphosphate; Cholesterol; D-Glucose (Dextrose); Glutathione (reduced); Guanine hydrochloride; Hypoxanthine Na; Phenol Red; Ribose; Sodium Acetate; Thymine; Tween 80®; Uracil; and Xanthine-Na. In some embodiments, the basal media is Medium 199.

In some embodiments, the basal media comprises platelet-derive growth factor (PDGF) (e.g., PDGF-BB, PDGF-AB, and PDGF-AA), a lipid (e.g., stearic acid, myristic acid, oleic acid, linoleic acid, palmitic acid, palmitoleic acid, arachidonic acid, linolenic acid, cholesterol, alpha-tocopherol acetate), bone morphogenic protein (BMP) (e.g., BMP-4 or BMP-6), TGF-β (e.g., TGF-β1, TGF-β2, TGF-β3), insulin-like growth factor (IGF), hydrocortisone, fibronectin, bFGF, albumin, insulin, FBS, or any combinations thereof.

In some embodiments, the tri-component matrix comprises type II collagen (e.g., isolated and purified non-denatured type II collagen). In some embodiments, the type II collagen is non-denatured. In some embodiments, the tri-component matrix further comprises type VI, type IX, type X, type XI and/or type XIII collagen.

In some embodiments, the type II collagen is derived from any suitable source. In some embodiments, the type II collagen is derived from a non-mammalian vertebrate (e.g., a shark). In some embodiments, the type II collagen is derived from a mammal. In some embodiments, the type II collagen is derived from a human. In some embodiments, the type II collagen is derived from a non-human mammal. In some embodiments, the type II collagen is bovine-derive, equine-derive, or porcine-derived. In some embodiments, the type II collagen is bovine-derived type II collagen.

In some embodiments, the concentration of type II collagen is from about 0.1 mg/ml to about 50 mg/ml. In some embodiments, the concentration of type II collagen is from about 0.5 mg/ml to about 25 mg/ml. In some embodiments, the concentration of type II collagen is from about 1 mg/ml to about 10 mg/ml. In some embodiments, the concentration of type II collagen is from about 1 mg/ml to about 5 mg/ml. In some embodiments, the concentration of type II collagen is about 3 mg/ml.

Hyaluronan (also referred to as hyaluronic acid or HA) is an anionic, nonsulfated glycosaminoglycan. It is composed on disaccharides, composed of D-glucuronic acid and D-N-acetylglucosamine, linked via alternating β-1,4 and β-1,3 glycosidic bonds. The size of hyaluronan varies. Hyaluronans have been found with 25,000 disaccharide repeats. They range in size from 5,000 to 20,000,000 Da in vivo. The average molecular weight in human synovial fluid is 3-4 million Da, and hyaluronan purified from human umbilical cord is 3,140,000 Da.

In some embodiments, the tri-component matrix comprises high molecular weight hyaluronan (i.e., greater than about 1000 Da). In some embodiments, the tri-component matrix comprises low molecular weight hyaluronan (i.e., less than about 1000 Da). In some embodiments, the tri-component matrix comprises hyaluronan having a size from about 500 Da to about 20,000,000 Da. In some embodiments, the tri-component matrix comprises hyaluronan having a size from about 500 to about 5000 Da. In some embodiments, the tri-component matrix comprises hyaluronan having a size from about 80,000 to about 800,000 Da. In some embodiments, the tri-component matrix comprises hyaluronan having a size of about 1000 to about 15,000,000 Da. In some embodiments, the tri-component matrix comprises hyaluronan having a size of about 2000 to about 10,000,000 Da. In some embodiments, the tri-component matrix comprises hyaluronan having a size of about 3000 to about 7,500,000 Da. In some embodiments, the tri-component matrix comprises hyaluronan having a size of about 4000 to about 5,000,000 Da. In some embodiments, the tri-component matrix comprises hyaluronan having a size of about 5000 to about 2,500,000 Da. In some embodiments, the tri-component matrix comprises hyaluronan having a size of about 6000 to about 1,000,000 Da. In some embodiments, the tri-component matrix comprises hyaluronan having a size of about 7000 to about 900,000 Da. In some embodiments, the tri-component matrix comprises hyaluronan having a size of about 8000 to about 800,000 Da. In some embodiments, the tri-component matrix comprises hyaluronan having a size of about 9000 to about 700,000 Da. In some embodiments, the tri-component matrix comprises hyaluronan having a size of about 10,000 to about 600,000 Da. In some embodiments, the tri-component matrix comprises hyaluronan having a size of about 15,000 to about 500,000 Da. In some embodiments, the tri-component matrix comprises hyaluronan having a size of about 20,000 to about 400,000 Da. In some embodiments, the tri-component matrix comprises hyaluronan having a size of about 25,000 to about 300,000 Da. In some embodiments, the tri-component matrix comprises hyaluronan having a size of about 30,000 to about 200,000 Da. In some embodiments, the tri-component matrix comprises hyaluronan having a size of about 35,000 to about 200,000 Da. In some embodiments, the tri-component matrix comprises hyaluronan having a size of about 40,000 to about 100,000 Da. In some embodiments, the tri-component matrix comprises hyaluronan having a size of about 50,000 to about 100,000 Da.

In some embodiments, the concentration of hyaluronan is from about 0.1 mg/ml to about 25 mg/ml. In some embodiments, the concentration of hyaluronan is from about 0.25 mg/ml to about 10 mg/ml. In some embodiments, the concentration of hyaluronan is from about 0.25 mg/ml to about 5 mg/ml. In some embodiments, the concentration of hyaluronan is from about 0.25 mg/ml to about 3 mg/ml. In some embodiments, the concentration of hyaluronic acid is about 1 mg/ml.

Chondroitin sulfate is a sulfated glycosaminoglycan (GAG) composed of a chain of alternating sugars: N-acetyl-D-galactosamine (GalNAc) and D-glucuronic acid (GlcA). In certain instances, chondroitin chains have over 100 individual sugars, each of which can be sulfated in variable positions and quantities. Chondroitin sulfate is a structural component of cartilage. The tightly packed and highly charged sulfate groups of chondroitin sulfate generate electrostatic repulsion that provides much of the resistance of cartilage to compression. The site of sulfation varies amongst chondroitin chains Chondroitin sulfate A is sulfated on carbon 4 of the N-acetylgalactosamine (GalNAc) sugar. Chondroitin sulfate C is sulfated on carbon 6 of the GalNAc sugar. Chondroitin sulfate D is sulfated on carbon 2 of the glucuronic acid and 6 of the GalNAc sugar. Chondroitin sulfate E is sulfated on carbons 4 and 6 of the GalNAc sugar.

In some embodiments, the tri-component matrix comprises any suitable chondroitin sulfate. In some embodiments, the tri-component matrix comprises Chondroitin sulfate A, Chondroitin sulfate C, Chondroitin sulfate D, and/or Chondroitin sulfate E.

In some embodiments, the concentration of chondroitin sulfate is from about 0.1 mg/ml to about 25 mg/ml. In some embodiments, the concentration of chondroitin sulfate is from about 0.25 mg/ml to about 10 mg/ml. In some embodiments, the concentration of chondroitin sulfate is from about 0.25 mg/ml to about 5 mg/ml. In some embodiments, the concentration of chondroitin sulfate is from about 0.25 mg/ml to about 3 mg/ml.

In some embodiments, the tri-component matrix is a medium for the ingrowth of native chondrocytes. In some embodiments, the matrix further comprises chondrocytes either prior to or following implantation in vivo. In some embodiments, the matrix is impregnated with chondrocytes immediately prior to implantation in a subject, e.g. by injection.

In some embodiments, the tri-component matrix further comprises additional additives. In some embodiments, additional additives included in the tri-component matrix include, for example, chondronectin, laminin, fibronectin, calcium alginate, anchorin II, biglycan, decorin, versican, fibromodulin, lumican, bone, cartilage cell growth-promoting hormones, and growth factors such as cartilage inducing factor (CIP), insulin-like growth factor (IGF), IGF-1, transforming growth factor [beta] (TGFß), TGF-ß1, osteogenic protein-1 (OP-1) and bone morphogenetic factors (BMPs) such as native or recombinant human BMP-2, BMP-3 (osteogenin), BMP-4, BMP-7, BMP-8, bFGF, CDMP or other skeletal matrix molecules, as well as signaling peptides such as vascular endothelial growth factor (EGF/VEGF), parathyroid hormone related protein (PTHrP) and platelet derived growth factor (PDGF). In some embodiments, nucleic acid sequences (e.g., mammalian expression vectors) encoding any of the above listed additional additives, or which are capable of inducing or promoting in vivo production of the above listed additional additives, is incorporated into the tri-component matrix material.

In some embodiments, the tri-component matrix further comprises an active agent. In some embodiments, the tri-component matrix further comprises an antibacterial agent, e.g., taurolidine, taurultam, or antibiotics such as tetracyclines and gentamycins. In some embodiments, the tri-component matrix further comprises an anti-inflammatory agent. In some embodiments, the tri-component matrix further comprises an NSAID. In some embodiments, the tri-component matrix further comprises celecoxib, oxaprozin, salsalate, diflunisal, indomethacin, meloxicam, ketorolac, diclofenac, naproxen, sulindac, tenoxicam, etodolac, nabumetone, piroxicam, carprofen, flubiprofen, ibuprofen, aspirin, paracetamol, or any combinations thereof. In some embodiments, the tri-component matrix further comprises a steroid, e.g., cortisone, hydrocortisone, prednisone, prednisolone, solumedrol, triamcinolone, kenalog, celestone, and depomedrol. In some embodiments, the tri-component matrix further comprises a disease-modifying anti-rheumatic drug (DMARD). In some embodiments, the tri-component matrix further comprises abatacept, adalimumab, azathioprine, chloroquine, hydroxychloroquine, Cyclosporin A, D-penicillamine, etanercept, golimumab, infliximab, leflunomide, methotrexate, minocycline, rituximab, sulfasalazine, or any combinations thereof.

In some embodiments, the tri-component matrix further comprises an agent that prevents or reduces vascularization. Examples of agents that prevent or reduce vascularization include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists, and antibodies to VEGF.

In some embodiments, the tri-component matrix disclosed herein elicits less of an inflammatory response than an alginate matrix.

Methods of Culturing Cells

The present invention also provides a method for culturing cells, comprising culturing cells in a tri-component matrix, as disclosed herein, comprising a) isolated and purified non-denatured type II collagen; b) hyaluronan; and c) chondroitin sulfate. In some embodiments, the cells within the tri-component matrix are cultured in a tissue culture vessel. In some embodiments, the tissue culture vessel is tissue culture-grade plastic. In some embodiments, the plastic is polystyrene. In some embodiments, the tissue culture vessel is glass.

In some embodiments, the tri-component matrix further comprises a cell-culture media. In some embodiments, the cell-culture media is a basal media. In some embodiments, the basal media is Medium 199, DMEM (for example, DMEM supplemented with fetal bovine serum), RPMI-1640, Ham's F-12, or any combinations thereof. In some embodiments, the basal media is a chondrocyte basal medium. In some embodiments, the basal media comprises the following components: Glycine; L-Alanine; L-Arginine hydrochloride; L-Aspartic acid; L-Cysteine hydrochloride-$H_2O$; L-Cystine 2HCl; L-Glutamic Acid; L-Glutamine; L-Histidine hydrochloride-$H_2O$; L-Hydroxyproline; L-Isoleucine; L-Leucine; L-Lysine hydrochloride; L-Methionine; L-Phenylalanine; L-Proline; L-Serine; L-Threonine; L-Tryptophan; L-Tyrosine disodium salt dehydrate; L-Valine; Alpha-tocopherol Phosphate; Ascorbic Acid; Biotin; Choline chloride; D-Calcium pantothenate; Folic Acid; Menadione (Vitamin K3); Niacinamide; Nicotinic acid (Niacin); Para-Aminobenzoic Acid; Pyridoxal hydrochloride; Pyridoxine hydrochloride; Riboflavin; Thiamine hydrochloride; Vitamin A (acetate); Vitamin D2 (Calciferol); i-Inositol; Calcium Chloride ($CaCl_2$) (anhyd.); Ferric nitrate (Fe$(NO_3)$-$9H_2O$); Magnesium Sulfate ($MgSO_4$) (anhyd.); Potassium Chloride (KCl); Sodium Bicarbonate ($NaHCO_3$); Sodium Chloride (NaCl); Sodium Phosphate monobasic ($NaH_2PO_4$—$H_2O$); 2-deoxy-D-ribose; Adenine sulfate; Adenosine 5'-phosphate; Adenosine 5'-triphosphate; Cholesterol; D-Glucose (Dextrose); Glutathione (reduced); Guanine hydrochloride; Hypoxanthine Na; Phenol Red; Ribose; Sodium Acetate; Thymine; Tween 80®; Uracil; and Xanthine-Na. In some embodiments, the basal media is Medium 199.

In some embodiments, the basal media comprises platelet-derive growth factor (PDGF) (e.g., PDGF-BB, PDGF-AB, and PDGF-AA), a lipid (e.g., stearic acid, myristic acid, oleic acid, linoleic acid, palmitic acid, palmitoleic acid, arachidonic acid, linolenic acid, cholesterol, alpha-tocopherol acetate), bone morphogenic protein (BMP) (e.g., BMP-4 or BMP-6), TGF-β (e.g., TGF-β1, TGF-β2, TGF-β3), insulin-like growth factor (IGF), hydrocortisone, fibronectin, bFGF, albumin, insulin, FBS, or any combinations thereof.

Methods of Use

Disclosed herein, in certain embodiments, are methods for inducing endogenous cartilage growth in a subject in need thereof, comprising implanting in the subject a tri-component matrix as disclosed herein, comprising a) isolated and purified non-denatured type II collagen; b) hyaluronan; and c) chondroitin sulfate. In some embodiments, the tri-component matrix further comprises chondrocytes and/or chondroprogenitor cells. In some embodiments, the method comprises injecting the tri-component into a cartilageonous area with a needle. In some embodiments, the method comprises injecting the tri-component matrix into a joint, e.g., a synovial joint. In some embodiments, the subject has a defect in cartilage (e.g., degeneration or absence of cartilage). In some embodiments, the subject has a cartilage related disorder. In some embodiments, the subject has osteoarthritis, rheumatoid arthritis, costochondritis, relapsing polychondritis, or any combinations thereof. In some embodiments, the subject has osteoarthritis. In some embodiments, the subject has rheumatoid arthritis. In some embodiments, the subject has damage to cartilage caused by a physical trauma.

In some embodiments, a tri-component matrix disclosed herein is used for methods of regenerating cartilaginous tissue. In some embodiments, the tri-component matrix further comprises chondrocytes, chondroprogenitor cells, mesenchymal stem cells, iPS cells, iPS cells derived from chondrocytes, H9-derived chondroprogenitor cells, Sox-9 transduced chondrocytes, osteoblasts, osteoprogenitors or any combinations thereof. In some embodiments, tri-component matrix is placed directly into an area of bone or cartilage defect. In some embodiments, the tri-component matrix is placed into an area of bone or cartilage defect with additional supportive biomaterial. In some embodiments, new cartilaginous tissue is formed. In some embodiments, the new cartilaginous tissue integrates with the tissue of the bone or cartilage defect. In some embodiments, the new cartilaginous tissue restores the surface of the cartilage or bone. In some embodiments, the new cartilaginous tissue comprises collagen type II. In some embodiments, the new cartilaginous tissue comprises superficial, intermediate, and deep zones characteristic of normal articular cartilage. In some embodiments, the superficial zone of the new cartilaginous tissue comprises lubricin. In some embodiments, the new cartilaginous tissue does not comprise teratomas, neoplastic cells, evidence of deformation, abnormal architectural features, or other inappropriate cell types.

Disclosed herein, in some embodiments, is a method of treating a cartilage-related disorder, comprising administration of a tri-component matrix, as described herein, to a site of cartilage injury or defect in a subject in need thereof. In some embodiments, the tri-component matrix further comprises chondrocytes, chondroprogenitor cells, mesenchymal stem cells, iPS cells, iPS cells derived from chondrocytes, H9-derived chondroprogenitor cells, Sox-9 transduced chondrocytes, osteoblasts, osteoprogenitors or any combinations thereof. In some embodiments, the cartilage-related disorder is articular cartilage trauma, meniscus injury, a chonodrogenesis disorder, arthritis, chondropathy, chondrosarcoma, chondromalacia, polychondritis, relapsing polychondritis, slipped epiphysis, osteochondritis dissecans, chondrodysplasia, costochondritis, osteochondroma, spondylosis, osteochondroses, Tietze syndrome, dermochondrocorneal dystrophy of Francois, epiphyseal dysplasia, carpotarsal osteochondromatosis, achondropasia, chondrocalcinosis, genochondromatosis, chondroma, achondrogenesis, echondromata, hyprochondroplasia, or Keutel syndrome. In some embodiments, the cartilage-related disorder is arthritis. In some embodiments, the arthritis is osteoarthritis. In some embodiments, the osteoarthritis occurs in the knee, finger, wrist, hip, spine, shoulder, elbow, toe, ankle, or neck of a subject.

Disclosed herein, in some embodiments, is a cartilage repair implant comprising a tri-component matrix as disclosed herein, further comprising chondrocytes, chondroprogenitor cells, mesenchymal stem cells, iPS cells, iPS cells derived from chondrocytes, H9-derived chondroprogenitor cells, Sox-9 transduced chondrocytes, osteoblasts, osteoprogenitors or any combinations thereof. In some embodiments, the cartilage repair implant further comprises an additional biomaterial substrate. Examples of additional biomaterials include: polyglycolic acid (PGA), polylactic acid, alginates (for example, the calcium salt), polyethylene oxide, fibrin adhesive, polylactic acid-polyglycolic acid copolymer, proteoglycans, glycosaminoglycans, human dermis, or a combination thereof. In some embodiments, proteoglycans and glycosaminoglycans are sulfated. In some embodiments, the additional biomaterial substrate is a membrane such as sheet, a porous body such as sponges, a mesh such as a knit, a textile, a non-woven fabric, cotton and the like. In some embodiments, the additional biomaterial is a porous material.

In some embodiments, the cartilage repair implant forms cartilage tissue and induces cartilaginous ossification. In some embodiments, ossification is also promoted by a growth factor which promotes bone formation, such as bone morphogenetic protein (BMP).

Prior to transplantation of the described cartilage therapy materials, it is preferable to prepare the area that is to be treated. For this purpose, the defect must be prepared to ensure that the implant will take more effectively (particularly as regards its attachment), to reduce the risks of vascularization, etc. Generally, the defect is treated in advance (in order to eliminate all defective cartilage from the area), then it is cleaned. Next, various implantation techniques can be implemented, according to the material being implanted (suspension, matrix, cartilage reconstituted in vitro).

Generally, implantation of the described cartilage therapy materials is performed by applying various surgical techniques known to the skilled person, such as affixing the implant during surgery, through biodegradable sutures or by the application of bioadhesives. Examples of bioadhesives include, notably, biological glues made of fibrin and/or thrombin, or other biocompatible materials. More particularly, the resorbable biocompatible film is affixed onto the area to be treated, by means of a biological or biocompatible glue. In a preferred variant, the film is positioned on the cartilaginous defect, then the pocket which is thus constituted is filled with cartilage therapy material.

In some embodiments, the method for inducing endogenous cartilage growth further comprises athroscopic lavage and/or debridement of the area where the implant will be administered. In some embodiments, part or all of the damaged cartilage is removed and a tri-component matrix (for example, the tri-component matrix further comprising chondrocytes or chondroprogenitor cells) is implanted (e.g., injected) into the area.

In some embodiments, the method for inducing endogenous cartilage growth further comprises marrow stimulating techniques (e.g., microfracture surgery). In some embodiments, (a) part or all of the damaged cartilage is removed from an area in need and underlying bone is partially or fully exposed, (b) microfractures are created in the subchondral bone (e.g., with the use of an awl), and (c) the tri-component matrix (for example, the tri-component matrix further comprising chondrocytes or chondroprogenitor cells) is implanted (e.g., injected) into the area.

In some embodiments, the tri-component matrix (for example, the tri-component matrix further comprising chondrocytes or chondroprogenitor cells) is injected with any suitable needle, e.g., a 16 gauge needle, 17 gauge needle, 18 gauge needle, 19 gauge needle, 20 gauge needle, 21 gauge needle, 22 gauge needle, 23 gauge needle, 24 gauge needle, 25 gauge needle, 26 gauge needle, 27 gauge needle, 28 gauge needle, 29 gauge needle, or a 30 gauge needle. In some embodiments, the tri-component matrix is injected with a 22 gauge needle. In some embodiments, the tri-component matrix is injected with a 25 gauge needle.

EXAMPLES

Example 1: Production of Tri-Component Matrix Comprising Chondrocytes

An exemplary method of manufacturing the tri-component matrix is as follows.

First, Bovine type II collagen was dissolved in 0.01 M acetic acid. Bovine Type II collagen (10 mg) was dissolved in in 2.4 ml 10 mM acetic acid O/N. 300 µl of 10× Medium 199 and 300 µl NaHCO$_3$/HEPES were added to the collagen/acetic acid mixture to neutralize.

330 µl of hyaluronic acid (HA at 10 mg/ml) (final concentration of 1 mg/ml) was added to the mixture.

60 µl of chondrotin sulfate (50 mg/ml, Bovine) was added to the mixture to a final concentration of 1 mg/ml to form the tri-component matrix.

Chondrocytes were then added to the tri-component matrix.

Example 2: Treatment of Osteochondral Defects with Chondroprogenitors Embedded in Alginate Using a surgical drill, 3-mm osteochondral defects were created in rabbit femoral trochlea grooves and condyles. The defects were repaired using two different treatments. As a control, nothing was implanted into one defect site. In the first treatment adult human chondrocyte derived chondroprogenitor cell pellets were embedded in alginate and then surgically implanted into the defect site. In the second treatment H9-derived chondroprogenitor cell pellets were embedded in alginate and then surgically implanted into the defect site.

Alginate was cross linked in the defect site using surgical gauze soaked with calcium chloride.

Figure 4:
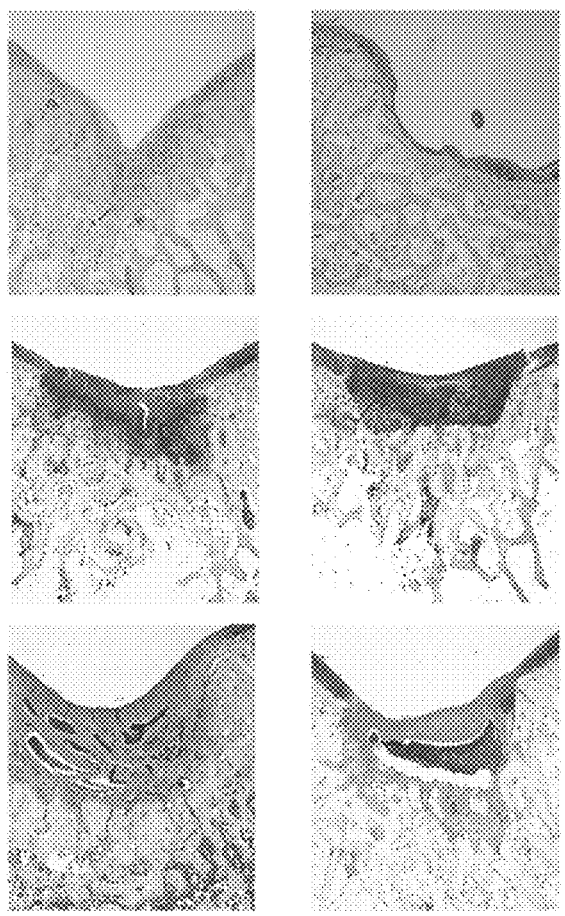
FIG. 4 exemplifies tissue repair by H9-derived chondroprogenitors and adult human chondrocyte derived chondroprogenitors. Cells were embedded in alginate prior to surgical implantation.

Histologic examination (FIG. 4) indicated that tissue repair generated by chondroprogenitors embedded in alginate was inferior to that generated by adult human chondrocyte derived chondroprogenitors embedded in alginate. However, both were superior to defects implanted with nothing.

Example 3: Treatment of Osteochondral Defects with Chondroprogenitors Embedded in Matrigel Using a surgical drill, 3-mm osteochondral defects were created in rabbit femoral trochlea grooves and condyles. The defects were repaired using four different treatments. As a control, nothing was implanted into one defect site. In the first treatment, as a control Matrigel alone was surgically implanted into the defect site. In the second treatment adult human chondrocyte derived chondroprogenitor cell pellets from donor #1 were embedded in Matrigel and then surgically implanted into the defect site. In the third treatment adult human chondrocyte derived chondroprogenitor cell pellets from donor #2 were embedded in Matrigel and then surgically implanted into the defect site. In the fourth treatment H9-derived chondroprogenitor cell pellets were embedded in Matrigel and then surgically implanted into the defect site.

Matrigel (BD Biosciences) was maintained as a liquid at 4 degrees Celsius and after implantation became gelatinous at 37 degrees Celsius.

Histologic examination (FIG. 1) indicated that tissue repair generated by H9-derived chondroprogenitors embedded in Matrigel was comparable to that generated by adult human chondrocyte derived chondroprogenitors embedded in Matrigel. However, both treatments were superior to defects implanted with nothing or with Matrigel alone.

Example 4: Treatment of Osteochondral Defects with Chondroprogenitors Embedded in Tri-Component Matrix Using a surgical drill, 3-mm osteochondral defects were created in rabbit femoral trochlea grooves and condyles. The defects were repaired using four different treatments. In all four treatments (adult human chondrocytes, H9 derives MSCs, iPSC derived from chondrocytes, and adult human MSCs) a tri-component matrix composed of collagen II, chondroitin sulfate, and hyaluronic acid was used.

The following protocol was used to assemble the tri-component matrix:
1) Bovine type II collagen (Innovative Research) was dissolved in 0.01 M acetic acid (add 10 mg of bovine type II collagen to 2.4 ml of 10 mM acetic acid, 300 µl of 10× Medium 199, and 300 µl of NaHCO$_3$/HEPES to neutralize the acetic acid);
2) 300 µg of hyaluronic acid was added at a concentration of 1 mg/ml;
3) 60 µg of chondrotin sulfate (bovine) was added at a concentration of 1 mg/ml;
4) The final concentration of the type II collagen is approximately 3 mg/ml.

Figure 2:
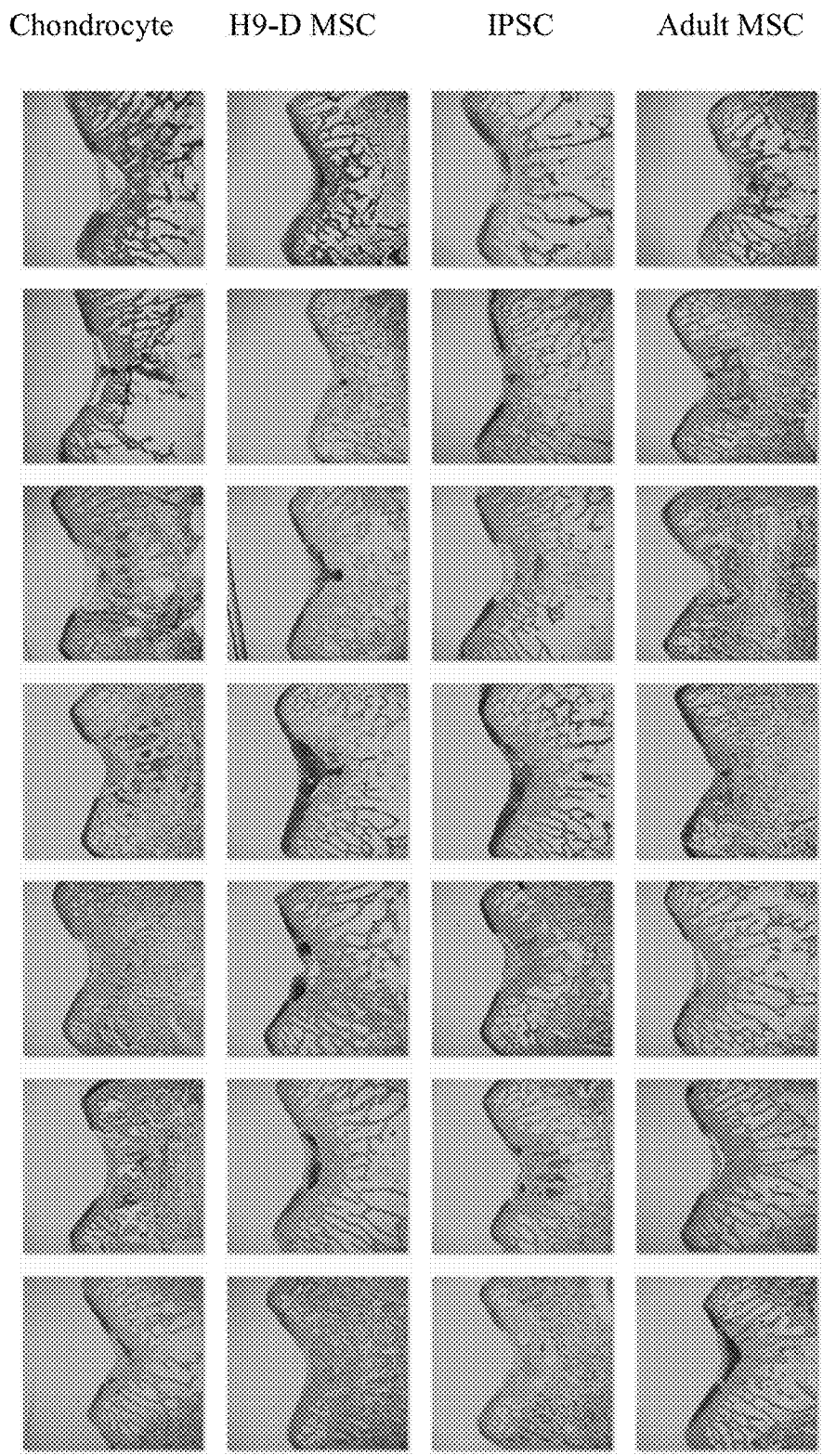
FIG. 2 exemplifies tissue repair by H9-derived chondroprogenitors (H9-D MSC), adult human chondrocytes (chondrocyte), pluripotent cell-derived chondroprogenitors (IPSC), and adult human mesenchymal stem cells (Adult MSC). Cells were embedded in a tri-component matrix of type II collagen, chondroitin sulfate, and hyaluronic acid prior to surgical implantation.
Figure 3:
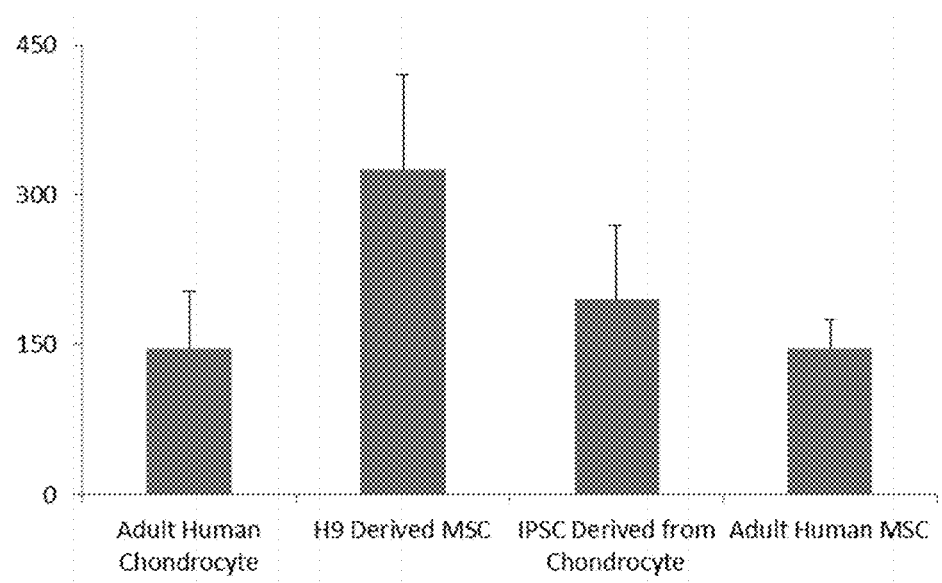
FIG. 3 exemplifies mechanical stiffness of tissue generated by H9-derived chondroprogenitors (H9 Derived MSC), adult human chondrocytes, pluripotent cell-derived chondroprogenitors (IPSC derived from chondrocyte), and adult human mesenchymal stem cells (Adult Human MSC) which had been embedded in a tri-component matrix of type II collagen, chondroitin sulfate, and hyaluronic acid prior to surgical implantation. The exemplified units are Newtons/mm.

Histologic examination (FIG. 2) indicated that tissue repair generated by H9-derived chondroprogenitors embedded in the tri-component matrix was better at tissue regeneration and had better mechanical properties (FIG. 3) than adult human chondrocyte derived chondroprogenitors, pluripotent cell-derived chondroprogenitors, and adult human mesenchymal stem cells.

Example 5: Clinical Study of Using Tri-Component Matrix in Treatment of Osteoarthritis Patients are given a single 5 mL injection of the tri-component matrix with chondrocytes (or a phosphate buffered saline control) into the synovial, with a possible repeat treatment after the week 16 visit.
Study Type: Interventional
Allocation: Randomized
Endpoint Classification: Safety/Efficacy Study
Intervention Model: Parallel Assignment
Masking: Double Blind (Subject, Outcomes Assessor)
Primary Purpose: Treatment
Outcome Measures:
Participants' assessment of pain. Mean scores were used for baseline (day 0) and for all visits up to week 16 (weeks 2, 4, 8, 12 and 16). The WOMAC Pain Subscale has a score range of 0-4, where 0=no pain and 4=extreme pain.

Participants categorized the pain they felt while walking using the WOMAC LK 3.1 A1 (Walking Pain) Subscale. The scale rates pain as none, mild, moderate, severe and extreme.

The change from baseline over the course of the 16-week initial treatment period using participants' assessment of physical function. Mean scores were used for baseline (day 0) and for all visits up to week 26 (weeks 4, 8, 12, 18 and 26). The WOMAC Function Subscale has a score range of 0-4 to assess the degree of difficulty completing tasks within the past 48 hours, where 0=no difficulty and 4=extreme difficulty.
Ages Eligible for Study: 40 Years and older
Genders Eligible for Study: Both
Accepts Healthy Volunteers: No
Inclusion Criteria:
Patient with documented diagnosis of primary osteoarthritis (OA) of the target knee made at least 3 months prior to trial.

Has radiographic evidence of OA in the tibio-femoral compartment of the target, knee with at least 1 definite osteophyte and a measureable joint space, as diagnosed by standard X-rays taken not longer than 3 months prior to Screening, and before any baseline assessment.

Has continued target knee pain despite conservative treatment (e.g. weight reduction, physical therapy, analgesics).

Has pain in the target knee as demonstrated by a score of 2 or 3 on the Western Ontario and McMaster Universities Osteoarthritis Index LikertZ Scale Version 3.1 (WOMAC LK 3.1) A1 (Walking Pain) Subscale.

Has a mean score of 1.5 to 3.5 on the Western Ontario and McMaster Universities Osteoarthritis Index Likert Scale Version 3.1 (WOMAC LK 3.1) A (Pain) Subscale.

Inclusion Criteria for Repeat Phase: Must have no major safety concerns during the first course of treatment as assessed by the Investigator; Must have a WOMAC LK 3.1 A score of at least 1.

Exclusion Criteria:

Has modified Kellgren-Lawrence Numerical Grading System of grade IV in the patello-femoral compartment of the target knee confirmed by standard X-rays taken not longer than 3 months prior to Screening, and before any baseline assessment.

Has clinically apparent tense effusion of the target knee.

Has had viscosupplementation in any joint including the target knee within 9 months prior to Screening.

Has concomitant inflammatory disease or other condition that affects the joints (e.g. rheumatoid arthritis, metabolic bone disease, psoriasis, gout, symptomatic chondrocalcinosis and active infection, etc.).

Symptomatic OA of the contralateral knee or of either hip that is not responsive to paracetamol and requires other therapy.

Has related hypersensitivities to avian proteins and/or any components of hyaluronan-based injection devices.

Example 6: Treatment of Osteoarthritis with Tri-Component Matrix Comprising Chondrocytes A patient presents with osteoarthritis in his knees. The calcified cartilage is removed from both knees. The surgeon creates fractures in the subchondral bone. The tri-component matrix with chondrocytes is injected into the knee. The patient returns to the doctor 4 weeks, 8 weeks, and 16 weeks later for an injection of the tri-component matrix with chondrocytes into both knees. The cartilage in the knees regenerates.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating a bone or cartilage defect in a subject in need thereof, comprising administering a transplantation composition at a site of the bone or cartilage defect, the transplantation composition comprising:
   a) a tri-component matrix, consisting of:
      i) isolated and purified non-denatured type II collagen at a concentration of 0.5 mg/ml to 5 mg/ml;
      ii) hyaluronan at a concentration of 1 mg/ml to 3 mg/ml; and
      iii) chondroitin sulfate at a concentration of 0.25 mg/ml to 3 mg/ml; and
   b) water; and
   c) a population of cells.

2. The method of claim 1, wherein the population of cells comprises chondrocytes, chondroprogenitor cells, induced pluripotent stem cells, mesenchymal stem cells, osteoblasts, osteoprogenitors, or combinations thereof.

3. The method of claim 1, wherein new tissue is produced.

4. The method of claim 3, wherein the new tissue restores a surface of the cartilage or bone.

5. The method of claim 3, wherein the new tissue comprises collagen type II.

6. The method of claim 3, wherein the new tissue comprises superficial, intermediate, and deep zones characteristic of normal articular cartilage.

7. The method of claim 3, wherein the new tissue does not comprise teratomas, neoplastic cells, evidence of deformation, abnormal architectural features, or other inappropriate cell types.

8. The method of claim 1, wherein the population of cells comprises chondrocytes.

9. The method of claim 1, wherein the population of cells comprises chondroprogenitor cells.

10. The method of claim 1, wherein the population of cells comprises induced pluripotent stem cells.

11. The method of claim 10, wherein the induced pluripotent stem cells are derived from chondrocytes.

12. The method of claim 9, wherein the chondroprogenitor cells are H9-derived chondroprogenitor cells.

13. The method of claim 8, wherein the chondrocytes are Sox-9 transduced chondrocytes.

14. The method of claim 1, wherein the bone or cartilage defect is associated with a cartilage-related disorder.

15. The method according to claim 14, wherein the cartilage-related disorder is articular cartilage trauma, meniscus injury, a chondrogenesis disorder, arthritis, chondropathy, chondrosarcoma, chondromalacia, polychondritis, relapsing polychondritis, slipped epiphysis, osteochondritis dissecans, chondrodysplasia, costochondritis, osteochondroma, spondylosis, osteochondrosis, Tietze syndrome, dermochondrocorneal dystrophy of Francois, epiphyseal dysplasia, carpotarsal osteochondromatosis, achondroplasia, chondrocalcinosis, genochondromatosis, chondroma, achondrogenesis, echondroma, hypochondroplasia, or Keutel syndrome.

16. The method of claim 15, wherein the cartilage-related disorder is arthritis.

17. The method of claim 16, wherein the arthritis occurs in a knee, finger, wrist, hip, spine, shoulder, elbow, toe, ankle, or neck of the subject.

18. The method of claim 1, wherein the population of cells does not comprise adult human bone marrow-derived mesenchymal stem cells.

19. The method of claim 1, wherein the transplantation composition is capable of being in a form of an injectable gel.

20. The method of claim 1, wherein the transplantation composition comprises fibrin.

* * * * *